United States Patent [19]

Pozzi et al.

[11] Patent Number: 4,869,900

[45] Date of Patent: Sep. 26, 1989

[54] PHARAMACEUTICAL COMPOSITION CONTAINING UBIDECARENONE

[75] Inventors: Franco Pozzi, Como; Antonio Longo, Monza; Angelo Carenzi, Busto Arsizio, all of Italy

[73] Assignee: Zambon S.p.A., Vicenza, Italy

[21] Appl. No.: 925,626

[22] PCT Filed: Jan. 31, 1986

[86] PCT No.: PCT/EP86/00046

§ 371 Date: Nov. 6, 1986

§ 102(e) Date: Nov. 6, 1986

[87] PCT Pub. No.: WO86/04503

PCT Pub. Date: Aug. 14, 1986

[30] Foreign Application Priority Data

Feb. 1, 1985 [IT] Italy ................................ 19353 A/85

[51] Int. Cl.$^4$ ............................................. A61K 37/48
[52] U.S. Cl. .................................. 424/94.1; 514/458; 514/682; 514/946
[58] Field of Search ............... 424/94.1; 514/946, 458, 514/682

[56] References Cited

U.S. PATENT DOCUMENTS 4,325,942 4/1982 Taki et al. ........................ 424/94.1
4,483,873 11/1984 Ohashi et al. ..................... 424/94.1
4,525,350 6/1985 Casey et al. ....................... 424/94.1

FOREIGN PATENT DOCUMENTS 0132821 of 0000 European Pat. Off. .

OTHER PUBLICATIONS

Eisai Co., Ltd., cited in Chem. Abstracts, vol. 100:145017d, 1984.
Handbook of Pharmaceutical Excipients, pp. 209–213.

Primary Examiner—Johnnie R. Brown
Assistant Examiner—Jacqueline M. Stone
Attorney, Agent, or Firm—Stevens, Davis, Miller & Mosher

[57] ABSTRACT

A pharmaceutical composition, comprising: Coenzyme $Q_{10}$ (ubidecarenone) 2–17% by weight; Lecithin 50–70% by weight; Surfactant agent 20–48% by weight. The surfactant agent has a melting point comprised between 35° and 55° C. and a HLB value from 12 to 15. Said composition provides a high absorption of Coenzime $Q_{10}$. Solid pharmaceutical preparations containing the above composition are described too.

11 Claims, No Drawings

PHARAMACEUTICAL COMPOSITION CONTAINING UBIDECARENONE

The present invention concerns a pharmaceutical composition containing Coenzyme $Q_{10}$ as active ingredient and more particularly it concerns an orally administerable composition which ensures a high bioavailability of the active ingredient.

Coenzyme $Q_{10}$ (ubidecarenone) of formula:

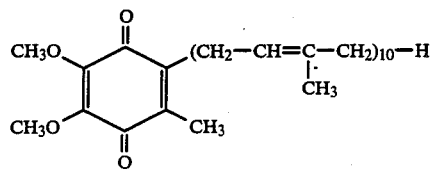

is a substance naturally occuring in mammals and man wherein it plays an important role in the mitochondrial electron transport. Coenzyme $Q_{10}$ (hereinafter referred to as $CoQ_{10}$) proved to be clinically effective in the treatment of several cardiac affections such as cardiac deficiency, ischemic disease, etcetera. However, $CoQ_{10}$ is very little soluble in water and in the gastric and intestinal juice; its absorption, notoriously scarce, takes place throught the lymphatic system.

Because of these characteristics, having available a pharmaceutical preparation ensuring an improved absorption of the drug is a very felt need.

Some pharmaceutical preparations or compositions having the scope of improving the absorption and thus the bioavailability of $CoQ_{10}$ have been described in the literature.

Among these, may be cited compositions containing $CoQ_{10}$ in association with a hydrophilic surfactant and a fatty acid (Japanese patent application No. 84/148718, Fujisawa Pharmaceutical Co. (Chemical Abstracts, 101, 226447c)), with an ester of a fatty acid with polyglycols and a water-soluble polymer (Japanese patent application No. 84/51214, Taiho Pharmaceutical Co. (Chemical Abstracts, 101, 137025k)) with a higher fatty acid and/or a monoglyceride of a higher fatty acid (European patent application No. 23349, Eisai Co.).

Liquid drinkable or injectable pharmaceutical compositions have also been described as well as aqueous emulsions containing $CoQ_{10}$ in association with hydrogenated lecithin (European patent application No. 83108, Eisai Co.) and with lecithin and methanol (Japanese patent application No. 78/56315, Eisai Co. (Chemical Abstracts, 89, 95002b)).

However, because of the characteristics of the drug and for practical purposes in connection to the administration to the patient, solid orally administerable pharmaceutical preparations are preferred.

We have now found, and this is an object of the present invention, an orally administerable composition as below specified, which affords a high absorption of $CoQ_{10}$.

The composition object of the present invention comprises (by weight) from 2 to 17% of $CoQ_{10}$, from 50 to 70% of lecithin and from 20 to 48% of a surfactant agent as below defined, the total being 100%.

Specific examples of compositions according to the invention are reported in the following table 1.

TABLE 1

Compositions according to the invention.

| Ingredient (% b.w.) | a | b | c | d | e | f |
|---|---|---|---|---|---|---|
| CoQ$_{10}$ | 2 | 5 | 7 | 10 | 16.7 | 17 |
| Lecithin | 70 | 65 | 63 | 70 | 63.3 | 55 |
| Surfactant agent | 48 | 30 | 30 | 20 | 20 | 28 |

Preferably lecithin is used in amounts of from 60 to 70% b.w. and the surfactant agent in amounts of from 20 to 30% b.w.

As lecithin, soybean lecithin is generally used but it may also be used, with identical results, lecithin of other sources.

The surfactant agent useful in the compositions object of the invention consists of a physical or chemical association of a surfactant with a fat or with polyethyleneglycol; said surfactant agent being characterized by a melting point comprised between 35° and 55° C. and by a HLB value (hydrophilic-lipophilic balance) comprised between 12 and 15 but preferably between 12 and 14.

An example of a suitable surfactant agent is the product "Gelucire 50/13" (trademark of Gattefosse Company) consisting of a mixture of mono-, di- or triglycerides of hydrogenated palmil and palmitate-stearate esters of polyethyleneglycol having a molecular weight between 1000 and 2000, a melting point of 50° C. and a HLB value of 13.

Another useful surfactant agent is the product "Glucire 44/14" (trademark of Gattefosse Company) consisting of glyceryl and polyethyleneglycol 1500 esters of copra hydrogenated oil fatty acids and palm kernel hydrogenated oil fatty acids having a melting point of 44° C. and HLB value of 14.

In experiments carried out on dogs (see example 8) the compositions object of the invention proved to be effective in ensuring a high bioavailability of $CoQ_{10}$.

The amount of absorbed product resulted to be noteworthy higher than that absorbed by administration of traditional preparations. The high bioavailability of $CoQ_{10}$, obtained by the compositions of the invention, appears to be strictly dependent on the contemporaneous presence of both the other components (lecithin and surfactant agent). In fact, compositions containing $CoQ_{10}$ in association with lecithin only or with the surfactant agent only, provided decidedly lower bioavailability levels (see example 8). The preparation of the compositions of the invention does not require complicated technologies or a specific apparatus; it is easily carried out by melting at 60° C. $CoQ_{10}$ into the surfactant agent and by then admixing the whole into the lecithin kept under stirring at 50° C. The procedure is preferably carried out in the dark and in a nitrogen atmosphere.

If desired, it is possible to add to the composition other additives which have a different function such as antioxidants e.g. tocopherols, ascorbic acid, BHT (butyl-hydroxy-toluene), BHA (butyl-hydroxy-anisole), gallates (esters of gallic acid), citric acid and mixtures thereof; metal sequestrants e.g. EDTA and flavours.

Said additives, which do not have any effect on the bioavailability of the drug, will be added in amounts comprised between 0.05 and 0.5% by weight with respect to the composition.

From the composition object of the present invention it is possible to prepare various solid pharmaceutical preparations.

The melt may be directly filled into hard or soft gelatin capsules.

Alternatively, the melt may be adsorbed on inert materials such as silica (colloidal), mannitol, lactose, starch, cellulose and magnesium stearate. When desired, the melt mixture of $CoQ_{10}$ and surfactant agent may be adsorbed on an inert material and thereafter admixed with lecithin.

The granular formulate thus obtained may be distributed in sachets or may be used, having previously added other additives such as disaggregants, lubricants and flavour ingredients in the preparation of tablets or chewable tablets.

The solid pharmaceutical preparation preferably contain in the unit dosage (capsule, tablet, sachet, chewing tablet) an amount of 10, 20 or 50 mg of $CoQ_{10}$.

The active ingredient in the compositions or pharmaceutical preparations according to the invention is stable for a long time. After one year at 30° C. no degradation of $CoQ_{10}$ was observed. It is evident to the man of the art how the carrier system consisting of lecithin and surfactant agent according to what is hereinabove described, may be useful also in the administration of other active ingredients having physico-chemical characteristics similar to those of $CoQ_{10}$ and more specifically of lipophilic, low-melting drugs having a scarce solubility in water.

Examples of such drugs include Vitamin E, Vitamin $K_1$ and $K_2$, tocopherols and derivatives thereof.

In order to better illustrate the invention, the following examples are given.

EXAMPLE 1

200 mg of a composition at 5% a.i. were prepared by melting 10 mg of $CoQ_{10}$ at 60° C. into 60 mg of "Gelucire 50/13" and by adding the melt to 130 mg of soybean lecithin kept under stirring at 50° C. The procedure was carried out in the dark and in a nitrogen atmosphere.

The resulting composition was then filled in gelatine capsules.

EXAMPLE 2

According to the procedure of Example 1, 300 mg of a composition at 5% a.i. of $CoQ_{10}$ with the same ingredients ratio, was prepared. The hot composition was poured on silica (200 mg) and lactose (1500 mg). After the adsorption, crospovidone (100 mg) and natural fruct flavouring (100 mg) were added.

The mixture was distributed in paper-aluminum-polyethylene sachets.

EXAMPLE 3

According to the procedure of Example 1, 300 mg of a composition at 7% a.i were prepared by melting 21 mg of $CoQ_{10}$ into 90 mg of "Gelucire 50/13" and by adding the melt to 189 mg of soybean lecithin.

The hot composition was then adsorbed on silica (180 mg) and mannitol (1000 mg). Crospovidone (100 mg), magnesium stearate (20 mg) and flavouring agents (100 mg) were then added.

The resulting powder was then prepared in the form of chewing tablets.

EXAMPLE 4

According to the procedure of Example 1, 300 mg of a composition at 16.6% a.i. were prepared by melting 50 mg of $CoQ_{10}$ into 60 mg of "Gelucire 50/13" and by adding the melt to 190 mg of soybean lecithin.

The resulting composition was then filled in gelatine capsules.

EXAMPLE 5

According to the procedure of Example 1, 300 mg of a composition at 16.67 a.i. were prepared by melting 50 mg of $CoQ_{10}$ into 60 mg of "Gelucire 44/14" and by adding the melt to 190 mg of soybean lecithin.

The resulting composition was then filled in gelatine capsules.

EXAMPLE 6

According to the procedure of Example 1, 1000 mg of a composition at 5% a.i. were prepared by melting 50 mg of $CoQ_{10}$ into 300 mg of "Gelucire 50/13" and by adding the melt to 60 mg of soybean lecithin.

The hot composition was then adsorbed on silica (400 mg) and sorbitole (1690 mg). A mixture of talc and magnesium stearate (60 mg) and flavouring agents (50 mg) was then added and the resulting powder was prepared in the form of chewable tablet.

EXAMPLE 7

Coenzyme $Q_{10}$ (50 mg) was melted at 60° C. into "gelucire 50/13" (100 mg) and the melt was adsorbed on sorbitole (1760 mg).

The resulting powder was admixed to soybean lecithin (350 mg) flavouring agents (65 mg) and lubricant (magnesium stearate and talc, 60 mg).

The resulting powder was prepared in the form of chewable tablet.

EXAMPLE 8

Male Beagle dogs, weighing 9–11 kg, overnight fast, were treated with 100 mg of $CoQ_{10}$. Four different formulations of $CoQ_{10}$ were used; each formulation was given to four animals. The blood was drawn immediately before the treatment and 1, 2, 3, 4, 6, 8, 24 hours after the drug administration.

Serum was separated by centrifugation, and the obtained samples were stored at −20° C. until they were analyzed.

Serum $CoQ_{10}$ concentration was evaluated using the method described by K. Abe et al. (J. Nutr. Sci. Vitaminol., 24, 555, 1978).

The AUC 0–24 h (Area Under Curve), calculated from the serum concentration vs. time curves, are reported in the table.

| Formulation[1] | $AUC_{0-24 h}$[2] (ng h ml$^{-1}$) | s.e.[3] | Dunnet t Test |
|---|---|---|---|
|  | 23884 | ±3643 |  |
| 2 | 31703 | ±4768 | t = 1.49[4] |
| 3 | 26674 | ±3297 | t = 0.53[4] |
| 4 | 52903 | ±1822 | t = 5.60 (P < 0.01) |

Notes
[1]Formulation 1 = capsule containing $CoQ_{10}$ granulate
Formulation 2 = capsule containing $CoQ_{10}$ plus surfactant (Gelucire 50/13")
Formulation 3 = capsule containing $CoQ_{10}$ plus lecithin
Formulation 4 = capsule containing the composition of example 1
[2]Mean of four experiments
[3]Standard error
[4]Not significant The above results clearly show how the serum concentration of $CoQ_{10}$ is not significantly increased by administration of $CoQ_{10}$ and surfactant agent only or of $CoQ_{10}$ and lecithin only but is significantly increased by administration of a composition according to the invention.

We claim:

1. An orally administerable pharmaceutical composition comprising from 2 to 17% by weight of Coenzyme $Q_{10}$ (ubidecarenone), from 50 to 70% by weight of lecithin and from 20 to 48% by weight of a surfactant agent consisting of a chemical or physical association of a surfactant with a fat or with polyethylene glycol, said surfactant agent having a melting point between 35° and 55° C. and an HLB value between 12 and 15.

2. A pharmaceutical composition according to claim 1, in which the lecithin is soybean lecithin.

3. A pharmaceutical composition according to claim 1, in which the surfactant agent consists of mono-, di- and triglycerides of hydrogenated palm oil and palmitate-stearate esters of polyethylene glycol having a molecular weight between 1000 and 2000, with melting point of 50° C. and an HLB value equal to 13.

4. A pharmaceutical composition according to claim 1, containing also from 0.05 to 0.5% by weight with respect to the composition weight, of antioxidants, metal sequestrants or mixtures thereof.

5. An orally administerable, solid pharmaceutical preparation containing a composition according to claim 1.

6. An orally administerable, solid pharmaceutical preparation containing a composition according to claim 4.

7. A pharmaceutical composition according to claim 1 containing an amount of lecithin between 60 and 70% by weight.

8. A pharmaceutical composition according to claim 1 containing an amount of surfactant agent between 20 and 30% by weight.

9. A pharmaceutical composition according to claim 1 in which the Coenzyme $Q_{10}$ is replaced by another active ingredient having physico-chemical characteristics similar to those of Coenzyme $Q_{10}$, and selected from the class consisting of Vitamin $K_1$ and $K_2$, tocopherols, and derivatives thereof.

10. A process for the preparation of a composition according to claim 1 comprising melting at 60° C. the Coenzyme $Q_{10}$ with the surfactant agent, and admixing the melt with the lecithin kept under stirring at 50° C.

11. A process according to claim 10 characterized in that the preparation of the composition is carried out in the dark and under nitrogen atmosphere.

* * * * *